United States Patent [19]

Church et al.

[11] Patent Number: 4,839,081
[45] Date of Patent: Jun. 13, 1989

[54] AUTOGENOUSLY HEATED LIQUID SOAP COMPOSITION

[75] Inventors: John A. Church, Princeton Junction; Umesh J. Mehta, South Plainfield, both of N.J.

[73] Assignee: Colgate-Palmolive Company, New York, N.Y.

[21] Appl. No.: 202,472

[22] Filed: Jun. 7, 1988

[51] Int. Cl.$^4$ ............................................. C11D 9/00
[52] U.S. Cl. ...................................... 252/108; 252/90; 252/94; 252/105; 252/121; 424/47; 514/846
[58] Field of Search ................... 252/90, 94, 105, 108, 252/121; 424/47; 514/846

[56] References Cited

U.S. PATENT DOCUMENTS

| | | | |
|---|---|---|---|
| 3,241,722 | 3/1966 | Nissen | 222/136 |
| 3,341,418 | 9/1969 | Moses et al. | 167/85 |
| 3,454,198 | 7/1969 | Flynn | 222/145 |
| 3,651,931 | 3/1972 | Hsiung | 424/47 |
| 3,702,302 | 11/1972 | Wilson | 252/70 |
| 3,722,752 | 3/1973 | Kenkare et al. | 222/145 |
| 3,819,524 | 6/1974 | Schubert et al. | 252/90 |
| 3,866,800 | 2/1975 | Schmitt | 222/94 |
| 4,088,751 | 5/1978 | Kenkare et al. | 424/47 |
| 4,110,426 | 8/1978 | Barnhurst et al. | 424/46 |
| 4,439,416 | 3/1984 | Cordon et al. | 424/47 |

Primary Examiner—Paul Lieberman
Assistant Examiner—Hoa V. Le
Attorney, Agent, or Firm—Robert Sullivan; Richard Ancel; Murray Grill

[57] ABSTRACT

A two-stage chemically heated liquid soap composition dispensed as a cleansing composition for the face and hands. The heating is derived from a novel double reductant and single oxidant redox system. Preferred active parts of the redox system are hydrogen peroxide and a combination of sodium sulfite and ascorbic acid with a suitable catalyst. The other components of the composition may change in accordance with the desired cleansing properties of the composition.

2 Claims, No Drawings

AUTOGENOUSLY HEATED LIQUID SOAP COMPOSITION

The present invention makes use of chemical heating with superior results for a hand or facial soap. A novel reductant/oxidant combination provides both instant and delayed heat release. The preferred oxidant is hydrogen peroxide, and the reductant may be an alkali metal sulfite in combination with an organic reductant such as ascorbic acid.

Cosmetic compositions such as face and beard preparation compositions for application to the skin or hair are often more effective for their intended purpose if they are applied hot. However, it is frequently inconvenient or difficult to provide them in heated form. While it is sometimes possible to mix them with hot water before use, it is necessary to have a supply of hot water available for this purpose. Moreover, when the compositions are supplied in ready-to-use form, particularly when they are supplied in a package with a liquefied gaseous propellant, the entire package must be heated, a procedure which is slow, difficult, and even dangerous under some conditions.

Self-heating two-part cosmetic compositions are well known in the art, for example as disclosed in U.S. Pat. Nos. 3,341,418; 3,702,302; 3,722,752; 3,819,524; 4,088,751; 4,110,426 and 4,439,416. However none of these prior art compositions incorporate more than one reductant, and they are thereby limited to only a single stage of heat release.

It has now been found that by providing a composition in two parts adapted to be mixed with each other during or immediately before use, one part containing an oxidant and the other a reductant combination, heat is evolved by reaction of the ingredients to produce both an instant and a sustained rise in the temperature of the mixture. By a sustained rise in temperature is meant an increase of at least 25° F. above room temperature lasting on the order of one minute after mixing at room temperature. While any suitable two-compartment container may be employed for such a package, the container in a preferred embodiment is a two-compartment pressurized container of a form which is known in the art. For example, the form of pressurized container and valve shown in U.S. Pat. Nos. 3,241,722 or 3,454,198 may be employed, the subject matters of which are incorporated by reference. The particular construction of the container forms no part of the present invention.

The exothermic or self-heating two-part aqueous cosmetic composition of the present invention may include suitable conventional ingredients. It is usually desirable that the part containing the reductant contain also all of the remaining ingredients except for a portion of the water. However, the part containing the oxidant may also include, in addition to a portion of the water, any of the remaining ingredients which are inert to the oxidant. When a liquefied gaseous propellant is present, it may be packaged with either part or even with both, depending upon the construction of the container and of the dispensing valve.

The ingredients commonly employed in cosmetic compositions such as shaving cream, hand cleanser and facial cleanser compositions include soaps, synthetic detergents including foaming agents, foam boosters, and germicides; fatty alcohols and acids, fatty oils and mineral oils, pigments and fillers, thickeners, astringents, emollients, solubilizers, humectants, alkalizing agents and buffers, etc. Any or all of the foregoing ingredients as well as other conventional ingredients may be present in the composition of the present invention.

OXIDANTS AND REDUCTANTS

The oxidizing agent or oxidant employed may be any one of a wide variety of materials depending upon the precise requirements of the particular composition in which it is used. Among the oxidants which may be used are hydrogen peroxide, urea hydrogen peroxide, sodium peroxide, sodium perborate, sodium persulfate, ammonium persulfate, potassium persulfate, and mixtures of any two or more of the foregoing in the form of aqueous solution. Generally, however, it will be preferred to use an aqueous solution of hydrogen peroxide as the oxidant.

Sodium sulfite as the reductant has the advantage of generating heat very rapidly when mixed with aqueous hydrogen peroxide, even when a catalyst is not present. However, such heat is very transient, i.e. it tends to dissipate in about 10 seconds or less, especially when the composition is rubbed between the hands or applied to the face. Ascorbic acid, on the other hand, characteristically reacts appreciably slower with hydrogen peroxide even when a catalyst is present. The use of ascorbic acid alone tends to give longer-lasting heat than sodium sulfite alone, but there is no initial rapid temperature rise as there is with sodium sulfite. By using a combination of the above two reductants, the advantages of both are obtained, i.e. an initial rapid temperature rise followed by a sustained release of heat leading to a pleasant continuing warmth effect on the hands or face.

Additional organic reductants which could be used instead of or in combination with ascorbic acid include, for example, 1,5-diethyl-2-thiobarbituric acid; 2,2'-thiodiethanol; and others. Oxidation of these may be catalyzed with known catalysts such as ammonium molybdate or sodium tungstate.

The quantity of oxidants and reductants present will depend in part upon how much heat is desired and in part upon the nature of the by-products which result from the reaction and their effect, if any, upon the desired properties of the composition. It is generally desirable that the total amount of reductant be at least as great as the amount required for stoichiometric reaction with all of the oxidants present.

GENERAL RANGE OF PREPARATION

The ingredients and their respective range of amounts in parts by weight is as follows: 60 to 70 parts of deionized water; 10 to 20 parts of coco monoglyceride sulfate; 0.5 to 2.0 parts of soap, preferably 85 tallow-15 coconut oil soap; 2.0 to 4.0 parts of stearic acid; 3.0 to 7.0 parts of glycerine; 3.0 to 5.0 parts of sodium sulfite; 3.0 to 5.0 parts of ascorbic acid; 0.5 to 1.0 parts preservative such as Germaben II (diazolidinyl urea and paraben); 0.1 to 0.3 parts of catalyst, such as ammonium molybdate or sodium tungstate; 0.0 to 0.3 parts fragrance; and sufficient alkali such as 50% sodium hydroxide to adjust the pH to near neutrality.

An appropriate amount of the completed formulation is charged into a conventional aerosol can, together with a codispensing valve containing an aqueous hydrogen peroxide solution in a separate bag. Just before sealing the can by crimping the valve into position, an appropriate amount of volatile hydrocarbon propellant is added. Upon inverting the can and actuating the valve by fingertip pressure, a creamy foam of cleanser is dispensed which self-heats rapidly in the hand and maintains its heat for a significant period of time.

EXAMPLE OF PREPARATION

As a specific example, a two-stage self-heating soap composition was made up as follows:

To 66.53 parts of deionized water were added, in succession with stirring, 4.90 parts of glycerine; 14.71 parts of coco monoglyceride sulfate; 0.98 parts of an 85 tallow-15 coconut oil soap; and 2.94 parts of stearic acid. The whole was heated to 160°-170° F. with stirring and then cooled to 100° F., followed by addition of 0.50 parts of Germaben II preservative.

To this aqueous composition were then added 3.50 parts of sodium sulfite and 3.50 parts of ascorbic acid which were dissolved therein by stirring, as well as 0.24 parts of ammonium molybdate (catalyst for oxidation of ascorbic acid) and 0.24 parts of a proprietary fragrance composition. Then for pH adjustment, 1.96 parts of a 50% aqueous sodium hydroxide solution were added, all with thorough stirring.

A sample of 140 grams of this composition was added to a 45×150 mm aluminum one piece aerosol can, followed by addition of 3 grams of chilled isobutane to act as propellant. Immediately thereafter a codispensing plastic bag and valve assembly, wherein the plastic bag contained 32 grams of an 8.3% aqueous hydrogen peroxide solution, was placed in the can aperture and sealed by mechanical crimping. The sealed can was then shaken to emulsify and disperse the propellant.

Upon actuating the valve with a fingertip, the can dispensed a pleasant foam of cleanser, which heated in the hand in a noticeable 2-stage manner; there was an early flash of heat (due to the reaction of sodium sulfite with the peroxide), followed by a second stage of heat due to the catalyzed reaction of ascorbic acid with the peroxide.

A comparison test was made between the above formulation (Formulation A) and a formulation wherein the only reductant present was sodium sulfite (Formulation B). In Formulation B, instead of 3.5 parts sodium sulfite and 3.5 parts ascorbic acid, 7.1 parts of sodium sulfite were used. With ascorbic acid being omitted, there was no need for pH adjustment, and hence no 50% sodium hydroxide was added. Otherwise, the formulations were identical and were packaged the same way.

Formulations A and B were tested for duration of their autogeneously-generated heat in a practical sensory test, using five human volunteers, as follows. Each volunteer extended both hands, palms upwards. Into each hand was simultaneously dispensed Formulation A or Formulation B, and the volunteer was asked to close the fingers into the foam and slightly agitate the form to spread the heat. They were then asked which formulation gave the longer-lasting heating sensation. All five volunteers stated that Formulation A gave significantly longer-lasting heat than Formulation B.

We claim:

1. An autogenously two step heated liquid soap composition consisting essentially of a first component of glycerine in the amount by weight of between 3-7 parts, coco monoglyceride sulfate in the amount of between 10-20 parts, tallow coconut oil soap in the amount of between 0.5-2 parts, stearic acid in the amount of between 2-4 parts, alkali metal sulfite is in the amount of between 3-5 parts, ascorbic acid as an organic reductant in the amount of between 3-5 parts, a catalyst for oxidation of the organic reductant in the amount of between 0.1-0.3 parts and the balance of the said first component being pH-adjusted water, and a second component of hydrogen peroxide solution in an approximately stoichiometric amount with respect to the reductants said heating occurring when said first and second components are mixed.

2. An autogenously two step heated liquid soap composition consisting essentially of a first component of glycerine in the amount by weight of about 5 parts, coco monoglyceride sulfate in the amount of about 15 parts, tallow coconut oil soap in the amount of about one part, stearic acid in the amount of about 3 parts, alkali metal sulfite in the amount of about 3.5 parts, ascorbic acid as an organic reductant in the amount of about 3.5 parts, a catalyst for oxidation of the organic reductant in the amount of about 0.24 parts, and the balance of the first component is pH-adjusted water and a second component of hydrogen peroxide solution in an approximately stoichiometric amount with respect to the reductants said heating occurring when said first and second components are mixed.

* * * * *